United States Patent [19]

DeMarinis

[11] 4,013,765

[45] Mar. 22, 1977

[54] COMPOSITIONS AND METHODS FOR TREATING BACTERIAL INFECTIONS WITH SUBSTITUTED ACETAMIDOCEPHALOSPORINS

[75] Inventor: Robert M. DeMarinis, King of Prussia, Pa.

[73] Assignee: SmithKline Corporation, Philadelphia, Pa.

[22] Filed: Dec. 29, 1975

[21] Appl. No.: 644,475

Related U.S. Application Data

[62] Division of Ser. No. 428,536, Dec. 26, 1973, Pat. No. 3,957,770.

[52] U.S. Cl. .............................................. 424/246
[51] Int. Cl.² ....................................... A61K 31/54
[58] Field of Search ................ 424/246; 260/243 C

[56] References Cited

UNITED STATES PATENTS 3,828,037   8/1974   DeMarinis et al. ............ 260/243 C

*Primary Examiner*—Jerome D. Goldberg
*Attorney, Agent, or Firm*—Stuart R. Suter; William H. Edgerton; Alan D. Lourie

[57] ABSTRACT

Novel cephalosporins with the trifluoroethyl-mercaptoacetamido, trifluoroethylsulfinylacetamido, and trifluoroethylsulfonylacetamido groups at position 7 are prepared. These compounds have antibacterial activity.

20 Claims, No Drawings

COMPOSITIONS AND METHODS FOR TREATING BACTERIAL INFECTIONS WITH SUBSTITUTED ACETAMIDOCEPHALOSPORINS

This is a division of application Ser. No. 428,536, filed Dec. 26, 1973, now U.S. Pat. No. 3,957,770.

This invention relates to cephalosporin compounds with 2,2,2-trifluoroethylmercaptoacetamido group of the mono or dioxidized derivative thereof at position 7 of the cephem nucleus. These compounds have antibacterial activity.

A wide variety of acyl groups have been used at position 7 of the cephalosporin nucleus in the search for improved antibiotics. For example, 7-alkylmercaptoacetamidocephalosporanic acids have been disclosed in U.S. Pat. No. 3,297,692 and others. Also, 7-propargylmercaptoacetamidocephalosporins are disclosed in U.S. Pat. No. 3,278,531. In pending applications in which inventor is a coinventor, Ser. No. 249,858, 273,571, and 371,081, now U.S. Pat. Nos. 3,865,819; 3,828,037; and 3,880,848 respectively, trifluoromethylsulfonyl-; trifluoromethylsulfinyl- and trifluoromethylmercapto-acetamido cephalosporins are disclosed. Cephalosporins with trifluoroethylmercaptoacetamido or its oxidized derivatives in the 7-acyl moiety have not been previously described.

The compounds of this invention have the following structural formula

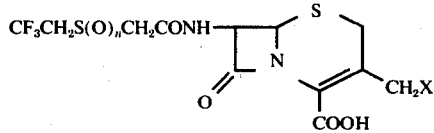

where $n$ is 0, 1, or 2;

X is hydrogen, acetoxy, $OCH_3$, $SCH_3$, or SHet; and

Het is a 5 or 6 membered heterocyclic ring containing carbon and 1-4 atoms selected from the group consisting of N, O, and S, unsubstituted or substituted with one or two substituents selected from the group consisting of alkyl of $C_1$-$C_6$, alkoxy of $C_1$-$C_6$, allyloxy, oxide, halogen, carbamyl, carboxyl, carbalkoxy of $C_1$-$C_6$, mercapto, methylthio, trifluoromethyl, hydroxy, amino, alkylamino and dialkylamino, each undefined alkyl having 1-6 carbon atoms.

Het includes the N-oxide derivatives of the heterocyclic systems named where such derivatives are possible, for example, pyridyl-N-oxide.

Preferred compounds are those where X is SHet. Particularly preferred are compounds where Het is tetrazolyl, triazolyl, thiadiazolyl, oxadiazolyl, or pyridyl, unsubstituted or substituted. Preferred substituents are alkyl of $C_1$-$C_6$, hydroxy or mercapto.

Also within the scope of the invention are the nontoxic pharmaceutically acceptable salts of the acidic compounds defined by the formula given above. Many salts and methods of preparation are known within the art. These include alkali metals, such as sodium or potassium, and ammonium salts including organic amines such as triethylamine and the like.

The compounds of the invention are prepared by acylation of a 7-aminocephalosporanic acid or a derivative thereof. The acylation agents are trifluoroethylmercaptoacetic acid, trifluoroethylsulfinylacetic acid, and trifluoroethylsulfonylacetic acid or their activated derivatives. Common methods to activate the carboxyl group, such as mixed anhydride, acid halide, or activated ester, are known to one skilled in the art and may be used. Also a coupling reagent such as dicyclohexylcarbodiimide or N,N'-carbonyldiimidazole may be used to acylate 7-aminocephalosporanic acid esters and derivatives thereof.

The 7-aminocephalosporanic acids and derivatives and methods for their preparation are well known in the cephalosporin art. General methods to prepare these compounds are in the book *Cephalosporins and Penicillins — Chemistry and Biology*, ed. Flynn, Academic Press, New York, 1972. Methods to prepare the 7-amino-3-heterocyclic-thiomethyl compounds are given in U.S. Pat. No. 3,516,997. Trifluoroethylmercaptoacetic acid is prepared by the reaction of 2,2,2-trifluoroethyl iodide and mercaptoacetic acid, both of which are commercially available, in the presence of a base, for example, sodium hydroxide. Oxidation with one or two moles of m-chloroperbenzoic acid gives the sulfinyl and sulfonyl derivatives, respectively. Preparation of the other acylation or activated derivatives is done by standard methods or described herein.

The compounds of this invention have broad-spectrum antibacterial activity with minimum inhibitory concentrations (MIC) ranging from 0.2 to >200 ug/ml when determined by standard agar inclusion methods. Table 1 shows MIC's for a variety of compounds within the scope of this invention against representative Gram-positive and Gram-negative bacteria.

The compounds of this invention are formulated and administered by injection in the same manner as other cephalosporins in dosages of from 250 to 1000 mg. The daily dosage, which may be divided, may range from 1-5 g and is dependent on the age and weight of the subject and on the infection being treated. The dosage can be determined by those skilled in the art based on the data disclosed herein and experience with known cephalosporins.

TABLE 1

| Compound Number * | MIC (μg/ml) | | | | |
|---|---|---|---|---|---|
| | 1 | 2 | 3 | 4 | 5 |
| S. aureus HH 127 | 0.4 | 0.2 | 0.2 | 1.6 | 3.1 |
| S. aureus SK 23390 | 0.4 | 0.1 | 0.1 | 0.8 | 3.1 |
| S. aureus Villaluz | 25 | 25 | 12.5 | 100 | 200 |
| Strep. faecalis HH 34358 | 25 | 6.3 | 12.5 | 100 | >200 |
| E. coli SK 12140 | 6.3 | 6.3 | 1.6 | 0.8 | 6.3 |
| E. coli HH 33779 | 50 | 12.5 | 6.3 | 3.1 | 12.5 |
| Kleb.pneumo. SK 4200 | 6.3 | 6.3 | 3.1 | 0.8 | 3.1 |
| Kleb.pneumo. SK 1200 | 3.1 | 3.1 | 1.6 | 0.4 | 3.1 |
| Salmonella ATCC 12176 | 6.3 | 6.3 | 0.8 | 1.6 | 6.3 |
| Shigella paradysentiae | 6.3 | 1.6 | 0.4 | 0.4 | 6.3 |
| Pseudo. aeruginosa HH63 | >200 | >200 | >200 | >200 | >200 |
| Serratia marc. ATCC 13880 | >200 | >200 | >200 | >200 | >200 |
| Entero. aerogenes | | | | | |

TABLE 1-continued

| Compound Number * | MIC (μg/ml) | | | | |
|---|---|---|---|---|---|
| | 1 | 2 | 3 | 4 | 5 |
| ATCC 13048 | 50 | 25 | 6.3 | 6.3 | 50 |

*See Table 2 for structures

TABLE 2

| Compound No. | n | X |
|---|---|---|
| 1 | 0 | acetoxy |
| 2 | 0 | 5-methyl-1,3,4-thiadiazol-2-ylthio |
| 3 | 0 | 1-methyltetrazol-5-ylthio |
| 4 | 1 | 1-methyltetrazol-5-ylthio |
| 5 | 2 | 1-methyltetrazol-5-ylthio |

The following examples illustrate the invention but are not to be construed as limiting the scope thereof.

PREPARATION 1

Trifluoroethylmercaptoacetic acid chloride

Thionyl chloride (21.9 g, 184 mmol) and trifluoroethylmercaptoacetic acid (15.9 g, 91 mmol) were stirred together overnight. The excess reagent was removed in vacuo and the product was distilled; bp 62°–68°/20 mm.

PREPARATION 2

N-Hydroxysuccinimidyl trifluoroethylsulfinylacetate

To a solution of trifluoroethylmercaptoacetic acid (8.7 g, 50 mmol) and N-hydroxysuccinimide (5.8 g, 50 mmol) in tetrahydrofuran (150 ml) was added dropwise a solution of dicyclohexylcarbodiimide (10.3 g, 50 mmol) in tetrahydrofuran (75 ml). The reaction was stirred overnight at room temperature. The solid urea was filtered and washed with THF, the filtrate was concentrated to 25 ml, and additional urea was removed. The solution was evaporated and the product was recrystallized from chloroform.

A solution of m-chloroperbenzoic acid (85%, 9.3 g, 46 mmol) in ether (100 ml) was added dropwise to a cold solution of N-hydroxysuccinimidyl trifluoroethylmercaptoacetate (12.5 g, 46 mmol) in chloroform (50 ml). The reaction was stirred 1 hour at ice bath temperature, allowed to warm to room temperature and stirred overnight. The solid product was collected and recrystallized from ethyl acetate.

PREPARATION 3

Trifluoroethylsulfonylacetic acid

To a cooled solution of methyl trifluoroethylmercaptoacetate (22.0 g, 177 mmol) in chloroform (75 ml) was added dropwise a solution of m-chloroperbenzoic acid (47.4 g, 234 mmol) in ether (300 ml). After addition was complete, the solution was allowed to warm to room temperature and stirred overnight. It was washed with saturated sodium bisulfite, 5% sodium bicarbonate and saturated sodium chloride. The organic phase was separated, dried over $MgSO_4$, filtered and evaporated to give 12.2 g of the sulfone. The sulfone ester was dissolved in 20 ml of methanol to which was added 200 ml of 3N HCl and the solution refluxed overnight. The solution was poured into 100 ml of ice water and extracted with ethyl acetate six times. The ethyl acetate was extracted three times with 5% sodium bicarbonate and the basic extract acidified and extracted again three times with ethyl acetate. The extracts were dried, filtered and evaporated to give 7.0 g of the title compound, mp 145°.

EXAMPLE 1

7-Trifluoroethylmercaptoacetamidocephalosporanic acid

A solution of 7-aminocephalosporanic acid (4.1 g, 15 mmol) in 1:1 acetone:5% sodium bicarbonate (125 ml) was cooled to −20° and then a solution of trifluoroethylmercaptoacetyl chloride (2.4 g, 12.5 mmol) in acetone (40 ml) was added dropwise over about a 30 minute period. The solution was maintained at about pH 8 by the addition of 5% NaOH as needed. The reaction was stirred at −20° for 20 minutes, −10° for 20 minutes, and room temperature for 1 hour. The reaction was diluted with water (50 ml), washed with ether (3 × 150 ml), acidified to pH 2 and extracted with ethyl acetate (3 × 150 ml). The extracts were washed with water, dried, and concentrated to give the product.

The sodium salt was prepared by dissolving the acid in ethyl acetate, adding a sodium 2-ethylhexanoate solution, and then slowly adding ether until the sodium salt of the title compound was precipitated.

EXAMPLE 2

7-Trifluoroethylmercaptoacetamido-3-(5-methyl-1,3,4-thiadiazol-2-ylthiomethyl)-3-cephem-4-carboxylic acid 7-Amino-3-(5-methyl-1,3,4-thiadiazol-2-ylthiomethyl)-3-cephem-4-carboxylic acid (3.96 g, 14 mmol) was reacted with trifluoroethylmercaptoacetyl chloride in the same manner as described in Example 1. After stirring at room temperature the solution was diluted with water (50 ml), washed with ether (3 × 150 ml), acidified to pH 2 with 3N HCl and extracted with ethyl acetate (3 × 150 ml). The extracts were washed with water, dried, and concentrated. The product was collected and converted to its sodium salt by the procedure in Example 1.

EXAMPLE 3

7-Trifluoroethylmercaptoacetamido-3-(1-methyltetrazol-5-ylthiomethyl)-3-cephem-4-carboxylic acid 7-Amino-3-(1-methyltetrazol-5-ythiomethyl)-3-cephem-4-carboxylic acid was acylated with trifluoroethylmercaptoacetyl chloride by the procedure of Example 2. The title product was converted into its sodium salt by the procedure described above.

EXAMPLE 4

When an equimolar amount of the following 7-amino-3-heterocyclicthiomethyl-3-cephem-4-carboxylic acids is substituted for 7-aminocephalosporanic acid in the procedure of Example 1, the corresponding 7-trifluoroethylmercaptoacetamido-3-heterocyclicthiomethyl-3-cephem-4-carboxylic acid is formed.

7-Amino-3-(tetrazol-5-ylthiomethyl)-3-cephem-4-carboxylic acid

7-Amino-3-(1,3,4-thiadiazol-2-ylthiomethyl)-3-cephem-4-carboxylic acid

7-Amino-3-(5-trifluoromethyl-1,3,4-thiadiazol-2-ylthiomethyl)-3-cephem-4-carboxylic acid 7-Amino-3-(5-ethyl-1,3,4-thiadiazol-2-ylthiomethyl)-3-cephem-4-carboxylic acid 7-Amino-3-(5-n-butyl-1,3,4-thiadiazol-2-ylthiomethyl)-3-cephem-4-carboxylic acid 7-Amino-3-(5-dimethylamino-1,3,4-thiadiazol-2-ylthiomethyl)-3-cephem-4-carboxylic acid 7-Amino-3-(5-mercapto-1,3,4-thiadiazol-2-ylthiomethyl)-3-cephem-4-carboxylic acid 7-Amino-3-(3-methylthio-1,2,4-thiadiazol-5-ylthiomethyl)-3-cephem-4-carboxylic acid 7-Amino-3-(3-methyl-1,2,4-thiadiazol-5-ylthiomethyl)-3-cephem-4-carboxylic acid 7-Amino-3-(1,2,4-triazol-3-ylthiomethyl)-3-cephem-4-carboxylic acid 7-Amino-3-(5-methyl-1,2,4-triazol-3-ylthiomethyl)-3-cephem-4-carboxylic acid 7-Amino-3-(4-methyl-1,2,4-triazol-3-ylthiomethyl)-3-cephem-4-carboxylic acid 7-Amino-3-(4,5-dimethyl-1,2,4-triazol-3-ylthiomethyl)-3-cephem-4-carboxylic acid 7-Amino-3-(2,5-dimethyl-1,2,4-triazol-3-ylthiomethyl)-3-cephem-4-carboxylic acid 7-Amino-3-(4-methyl-5-trifluoromethyl-1,2,4-triazol-3-ylthiomethyl)-3-cephem-4-carboxylic acid 7-Amino-3-(5-ethyl-1,2,4-triazol-3-ylthiomethyl)-3-cephem-4-carboxylic acid 7-Amino-3-(4-ethyl-1,2,4-triazol-3-ylthiomethyl)-3-cephem-4-carboxylic acid 7-Amino-3-(1-methyl-1,2,4-triazol-5-ylthiomethyl)-3-cephem-4-carboxylic acid 7-Amino-3-(1-methyl-1,2,4-triazol-3-ylthiomethyl)-3-cephem-4-carboxylic acid 7-Amino-3-(1-ethyl-1,2,4-triazol-5-ylthiomethyl)-3-cephem-4-carboxylic acid 7-Amino-3-(1-ethyl-1,2,4-triazol-3-ylthiomethyl)-3-cephem-4-carboxylic acid 7-Amino-3-(4-allyl-1,2,4-triazol-3-ylthiomethyl)-3-cephem-4-carboxylic acid 7-Amino-3-(5-methoxymethyl-1,2,4-triazol-3-ylthiomethyl)-3-cephem-4-carboxylic acid 7-Amino-3-(5-cyclopropyl-1,2,4-triazol-3-ylthiomethyl)-3-cephem-4-carboxylic acid 7-Amino-3-(5-bromo-1,2,4-triazol-3-ylthiomethyl)-3-cephem-4-carboxylic acid 7-Amino-3-(5-hydroxy-4-methyl-1,2,4-triazol-3-ylthiomethyl)-3-cephem-4-carboxylic acid 7-Amino-3-(5-hydroxy-4-ethyl-1,2,4-triazol-3-ylthiomethyl)-3-cephem-4-carboxylic acid 7-Amino-3-(5-hydroxy-1,2,4-triazol-3-ylthiomethyl)-3-cephem-4carboxylic acid 7-Amino-3-(1,2,3-triazol-4-ylthiomethyl)-3-cephem-4-carboxylic acid 7-Amino-3-(1-methyl-1,2,3-triazol-5-ylthiomethyl)-3-cephem-4-carboxylic acid 7-Amino-3-(4-methyl-1,2,3-triazol-5-ylthiomethyl)-3-cephem-4-carboxylic acid 7-Amino-3-(1,3,4-oxadiazol-2-ylthiomethyl)-3-cephem-4-carboxylic acid 7-Amino-3-(5-methyl-1,3,4-oxadiazol-2-ylthiomethyl)-3-cephem-4-carboxylic acid 7-Amino-3-(4-pyrimidylthiomethyl)-3-cephem-4-carboxylic acid 7-Amino-3-(2-pyrazinylthiomethyl)-3-cephem-4-carboxylic acid 7-Amino-3-(3-pyridylthiomethyl)-3-cephem-4-carboxylic acid 7-Amino-3-(4-pyridylthiomethyl)-3-cephem-4-carboxylic acid 7-Amino-3-(1-oxide-2-pyridylthiomethyl)-3-cephem-4-carboxylic acid.

EXAMPLE 5

7-Trifluoroethylsulfinylacetamido-3-(1-methyltetrazol-5-ylthiomethyl)-3-cephem-4-carboxylic acid Triethylamine (3.0 g, 30 mmol) was added to a suspension of 7-amino-3-(1-methyltetrazol-5-ylthiomethyl)-3-cephem-4-carboxylic acid (6.6 g, 20 mmol) in dimethylformamide (30 ml). After stirring 10 minutes, N-hydroxysuccinimidyl trifluoroethylsulfinylacetate (5.8 g, 20 mmol) was added. The reaction was stirred for 40 minutes and then poured into water (120 ml). The aqueous solution was washed with ethyl acetate, layered with fresh ethyl acetate and acidified to pH 2. The product was extracted with ethyl acetate which was washed with water, dried and concentrated. The precipitated product was collected and converted to its sodium salt.

EXAMPLE 6

Acylation of 7-aminocephalosporanic acid and 7-amino-3-(5-methyl-1,3,4-thiadiazol-2-ylthiomethyl)-3-cephem-4-carboxylic acid by the procedure of Example 5 gives 7-trifluoroethylsulfinylacetamidocephalosporanic acid and 7-trifluoroethylsulfinylacetamido-3-(5-methyl-1,3,4-thiadiazol-2-ylthiomethyl)-3-cephem-4-carboxylic acid.

EXAMPLE 7

When the 7-amino-3-heterocyclicthiomethyl-3-cephem-4-carboxylic acids enumerated in Example 4 are substituted for 7-amino-3-(1-methyltetrazol-5-ylthiomethyl)-3-cephem-4-carboxylic acid in the procedure of Example 5 the corresponding 7-trifluoroethylsulfinylacetamido-3-heterocyclicthiomethyl-3-cephem-4-carboxylic acid is obtained.

EXAMPLE 8

7-Trifluoroethylsulfonylacetamido-3-(1-methyltetrazol-5-ylthiomethyl)-3-cephem-4-carboxylic acid To a solution of t-butyl 7-amino-3-(1-methyltetrazol-5-ylthiomethyl)-3-cephem-4-carboxylate (7.2 g, 19 mmol) and trifluoroethylsulfonylacetic acid (3.9 g, 19 mmol) in tetrahydrofuran was added dropwise a solution of dicyclohexylcarbodiimide (3.9 g, 19 mmol) in tetrahydrofuran (100 ml). The reaction was stirred at room temperature overnight. The solution was filtered, concentrated to ca. 10 ml, filtered, and concentrated to a foam. The foam was dissolved in methylene chloride and the ester precipitated by the addition of cyclohexane.

The above ester (6.0 g, 10.6 mmol) was dissolved in acetonitrile (60 ml) and trifluoroacetic acid (60 ml) was added. The solution was stirred until tlc analysis indicated that the reaction was completed (ca. 3 hours). The solution was evaporated and the product was triturated with ether.

EXAMPLE 9

Acylation of the t-butyl esters of 7-aminocephalosporanic acid, 7-amino-3-(5-methyl-1,3,4-thiadiazol-2-ylthiomethyl-3-cephem-4-carboxylic acid, or any compound enumerated in Example 4 according to the procedure of Example 8 gives the corresponding t-butyl 7-trifluoroethylsulfonylacetamido-3-substituted-3-cephem-4-carboxylate which is hydrolyzed by the procedure of Example 8 to give the desired product.

EXAMPLE 10

Trifluoroethylsulfonylacetic acid is reacted with N-hydroxysuccinimide according to the procedure of Preparation 2 to give the activated ester which is reacted at once with 7-amino-3-(1,2,3-triazol-4-ylthiomethyl)-3-cephem-4-carboxylic acid to give 7-trifluoroethylsulfonylacetamido-3(1,2,3-triazol-4-ylthiomethyl)-3-cephem-4-carboxylic acid. 7-Trifluoroethylsulfonylacetamido-3-(4-methyl-1,2,3-triazol-5-ylthiomethyl)-3-cephem-4-carboxylic acid is prepared in a similar manner.

EXAMPLE 11

When 7-aminodesacetoxycephalosporanic acid (7-ADCA) is acylated according to the procedure of Example 1 with trifluoroethylmercaptoacetyl chloride and according to the procedure of Example 5 with N-hydroxysuccinimidyl trifluoroethylsulfinyl acetate, 7-trifluoroethylmercaptoacetamido-3-methyl-3-cephem-4-carboxylic acid and 7-trifluoroethylsulfinylacetamido-3-methyl-3-cephem-4-carboxylic acid are obtained.

When the t-butyl ester of 7-ADCA is acylated with trifluoroethylsulfonylacetic acid by the procedure of Example 8, 7-trifluoroethylsulfonylacetamido-3-methyl-3-cephem-4-carboxylic acid is obtained.

EXAMPLE 12

Using the procedure of Example 1, 7-amino-3-methoxymethyl-3-cephem-4-carboxylic acid is acylated with trifluoroethylmercaptoacetyl chloride to give 7-trifluoroethylmercaptoacetamido-3-methoxymethyl-3-cephem-4-carboxylic acid.

Acylation of 7-amino-3-methoxymethyl-3-cephem-4-carboxylic acid by the procedure of Example 5 gives 7-trifluoroethylsulfinylacetamido-3-methoxymethyl-3-cephem-4-carboxylic acid.

7-Trifluoroethylsulfonylacetamido-3-methoxymethyl-3-cephem-4-carboxylic acid is obtained when t-butyl 7-amino-3-methoxymethyl-3-cephem-4-carboxylate is acylated by the procedure of Example 8.

EXAMPLE 13

Substitution of 7-amino-3-methylmercaptomethyl-3-cephem-4-carboxylic acid or its t-butyl ester for 7-amino-3-methoxymethyl-3-cephem-4-carboxylic acid or its t-butyl ester in Example 12 gives the following products:
7-trifluoroethylmercaptoacetamido-3-methylmercaptomethyl-3-cephem-4-carboxylic acid
7-trifluoroethylsulfinylacetamido-3-methylmercaptomethyl-3-cephem-4-carboxylic acid
7-trifluoroethylsulfonylacetamido-3-methylmercaptomethyl-3-cephem-4-carboxylic acid

EXAMPLE 14

An injectable pharmaceutical composition is prepared by dissolving 100–500 mg of sodium 7-trifluoroethylsulfonylacetamido-3-(1-methyltetrazol-5-ylthiomethyl)-3-cephem-4-carboxylate in sterile water or sterile normal saline solution (1–2 ml). All other cephalosporins within the above disclosed formula including each compound enumerated in the above examples are formulated in a similar manner.

I claim:
1. An injectable pharmaceutical composition comprising a pharmaceutically acceptable carrier and an antibacterially effective amount of a compound of the formula

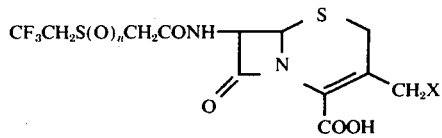

where
   $n$ is 0, 1, or 2;
   X is SHet; and
   Het is a 5 or 6-membered heterocyclic ring containing carbon and 1–4 atoms selected from the group consisting of N, O, and S, unsubstituted or substituted with one or two substituents selected from the group consisting of alkyl of $C_1$–$C_6$, alkoxy of $C_1$–$C_6$, allyloxy, oxide, halogen, carbamyl, carboxyl, carbalkoxy of $C_1$–$C_6$, mercapto, methylthio, trifluoromethyl, hydroxy, amino, alkylamino and dialkylamino, each undefined alkyl having 1–6 carbon atoms
or a non-toxic pharmaceutically acceptable salt thereof.

2. An injectable pharmaceutical composition as claimed in claim 1 where $n$ is 0.

3. An injectable pharmaceutical composition as claimed in claim 2 where X is SHet and Het is tetrazolyl, thiadiazolyl, triazolyl, oxadiazolyl, or pyridyl, unsubstituted or substituted with one or two substituents selected from the group consisting of alkyl of $C_1$–$C_6$, hydroxy, and mercapto.

4. An injectable pharmaceutical composition as claimed in claim 3 where the compound is 7-trifluoroethylmercaptoacetamido-3-(1-methyltetrazol-5-ylthiomethyl)-3-cephem-4-carboxylic acid.

5. An injectable pharmaceutical composition as claimed in claim 1 where $n$ is 1.

6. An injectable pharmaceutical composition as claimed in claim 5 where X is SHet and Het is tetrazolyl, thiadiazolyl, triazolyl, oxadiazolyl, or pyridyl, unsubstituted or substituted with one or two substituents selected from the group consisting of alkyl of $C_1$–$C_6$, hydroxy, and mercapto.

7. An injectable pharmaceutical composition as claimed in claim 6 where the compound is 7-trifluoroethylsulfinylacetamido-3-(1-methyltetrazol-5-ylthiomethyl)-3-cephem-4-carboxylic acid.

8. An injectable pharmaceutical composition as claimed in claim 1 where $n$ is 2.

9. An injectable pharmaceutical composition as claimed in claim 8 where X is SHet and Het is tetrazolyl, thiadiazolyl, triazolyl, oxadiazolyl, or pyridyl, unsubstituted or substituted with one or two substituents selected from the group consisting of alkyl of $C_1$–$C_6$, hydroxy, and mercapto.

10. An injectable pharmaceutical composition as claimed in claim 9 where the compound is 7-trifluoroethylsulfonylacetamido-3-(1-methyltetrazol-5-ylthiomethyl)-3-cephem-4-carboxylic acid.

11. A method of treating bacterial infections comprising administering by injection to a warm-blooded animal an effective but non-toxic dose of 250–1000 mg of a compound of the formula

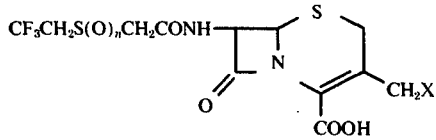

where
- $n$ is 0, 1, or 2;
- X is SHet; and
- Het is a 5 or 6-membered heterocyclic ring containing carbon and 1-4 atoms selected from the group consisting of N, O, and S, unsubstituted or substituted with one or two substituents selected from the group consisting of alkyl of $C_1$-$C_6$, alkoxy of $C_1$-$C_6$, allyloxy, oxide, halogen, carbamyl, carboxyl, carbalkoxy of $C_1$-$C_6$, mercapto, methylthio trifluoromethyl, hydroxy, amino, alkylamino and dialkylamino, each undefined alkyl having 1-6 carbon atoms or a non-toxic pharmaceutically acceptable salt thereof.

12. A method of treating bacterial infections as claimed in claim 11 where $n$ is 0.

13. A method of treating bacterial infections as claimed in claim 12 where X is SHet and Het is tetrazolyl, thiadiazolyl, triazolyl, oxadiazolyl, or pyridyl, unsubstituted or substituted with one or two substituents selected from the group consisting of alkyl of $C_1$-$C_6$, hydroxy, and mercapto.

14. A method of treating bacterial infections as claimed in claim 13 where the compound is 7-trifluoroethylmercaptoacetamido-3-(1-methyltetrazol-5-ylthiomethyl)-3-cephem-4-carboxylic acid.

15. A method of treating bacterial infections as claimed in claim 11 where $n$ is 1.

16. A method of treating bacterial infections as claimed in claim 15 where X is SHet and Het is tetrazolyl, thiadiazolyl, triazolyl, oxadiazolyl, or pyridyl, unsubstituted or substituted with one or two substituents selected from the group consisting of alkyl of $C_1$-$C_6$, hydroxy, and mercapto.

17. A method of treating bacterial infections as claimed in claim 16 where the compound is 7-trifluoroethylsulfinylacetamido-3-(1-methyltetrazol-5-ylthiomethyl)-3-cephem-4-carboxylic acid.

18. A method of treating bacterial infections as claimed in claim 11 where $n$ is 2.

19. A method of treating bacterial infections as claimed in claim 18 where X is SHet and Het is tetrazolyl, thiadiazolyl, triazolyl, oxadiazolyl, or pyridyl, unsubstituted or substituted with one or two substituents selected from the group consisting of alkyl of $C_1$-$C_6$, hydroxy, and mercapto.

20. A method of treating bacterial infections as claimed in claim 19 where the compound is 7-trifluoroethylsulfonylacetamido-3-(1-methyltetrazol-5-ylthiomethyl)-3-cephem-4-carboxylic acid.

* * * * *